United States Patent
Markwitz et al.

(10) Patent No.: US 9,633,541 B2
(45) Date of Patent: Apr. 25, 2017

(54) DISPLAY SYSTEM FOR TRACKING LARGE NUMBERS OF PERSONS AND/OR OBJECTS

(71) Applicant: TimeKeeping Systems, Inc., Solon, OH (US)

(72) Inventors: Barry J. Markwitz, Solon, OH (US); Paolo Argentieri, Richmond Heights, OH (US); Brent G. Bowers, Cuyahoga Falls, OH (US); Jason D. Doyle, Mantua, OH (US); John E. Hansley, II, Lyndhurst, OH (US); John W. Hoffman, Mentor, OH (US); Roger W. Stahl, Mantua, OH (US); Mary T. Upham, Brecksville, OH (US)

(73) Assignee: TimeKeeping Systems, Inc., Solon, OH (US)

( * ) Notice: Subject to any disclaimer, the term of this patent is extended or adjusted under 35 U.S.C. 154(b) by 0 days.

(21) Appl. No.: 13/987,206

(22) Filed: Jul. 12, 2013

(65) Prior Publication Data
US 2015/0015407 A1 Jan. 15, 2015

(51) Int. Cl.
*G08B 3/00* (2006.01)
*G08B 21/22* (2006.01)
*G06Q 10/00* (2012.01)

(52) U.S. Cl.
CPC ............ *G08B 21/22* (2013.01); *G06Q 10/00* (2013.01)

(58) Field of Classification Search
CPC .................... G08B 21/22; G06Q 10/00
USPC ........................................ 340/691.6
See application file for complete search history.

(56) References Cited

U.S. PATENT DOCUMENTS

| | | | |
|---|---|---|---|
| 7,646,307 B2 * | 1/2010 | Plocher et al. ............ | 340/573.1 |
| 8,560,580 B1 * | 10/2013 | Nacey ........................... | 707/825 |
| 2009/0048865 A1 * | 2/2009 | Breazeale, Jr. ................ | 705/2 |
| 2011/0074585 A1 * | 3/2011 | Harmon et al. ........... | 340/573.1 |
| 2014/0279628 A1 * | 9/2014 | Straznitskas ......... | G06Q 10/105 705/320 |

* cited by examiner

*Primary Examiner* — Kerri McNally
(74) *Attorney, Agent, or Firm* — James A. Hudak

(57) ABSTRACT

A display system for tracking large numbers of persons or objects in real-time is disclosed. The display system utilizes a tracking system that employs various types of technologies, such as RFID, to determine the location of the person and/or objects being tracked. The displays of the present invention utilize colors, graphics, and the physical groupings of related data on a display device, usually a computer monitor, to present tracking information in a compact, readily changeable, and easily analyzed format in real-time.

14 Claims, 16 Drawing Sheets
(16 of 16 Drawing Sheet(s) Filed in Color)

Fig. 2A

DISPLAY SYSTEM FOR TRACKING LARGE NUMBERS OF PERSONS AND/OR OBJECTS

TECHNICAL FIELD

The present invention relates, in general, to a tracking display system and, more particularly, to a display system for tracking large numbers of persons and/or objects in real-time.

BACKGROUND ART

The use of electronic systems to track the location of persons and/or objects of interest within institutions, such as prisons and/or healthcare facilities, is increasing significantly. Such systems can readily track large numbers of people and/or objects. All such systems generate accurate and detailed reports of the past movements of the persons and/or objects being tracked, however, it is desirable to show such movements and any problems associated with such movements at the time that they occur. Displaying such a large volume of information in real-time or near real-time to system users in a manner that is compact and easily analyzed creates an inherent problem in electronic tracking systems, however, such a display is required in order to maximize the usefulness of these systems.

In view of the inherent deficiencies associated with displays used for tracking large numbers of persons and/or objects, it has become desirable to develop a display for a tracking system that can readily present a very large volume of such information in real-time or near real-time in a manner that is compact and easily analyzed by the system user.

SUMMARY OF THE INVENTION

Tracking systems utilize various technologies to determine the location of persons and/or objects that are being tracked. Many such systems use a transponder, transceiver, or transmitter that is worn by or attached to a person or object that is being tracked and which transmits a unique identifier that is associated with the tracked person or object. Regardless of the technology utilized, such systems detect whether a tracked person and/or object is present at a particular location within a facility and provide data describing that location. Some tracking systems provide the locations by means of zone identifiers. A zone can be any defined area and, in practice, zones are usually defined so as to coincide with identified physical and/or functional areas within a facility, such as rooms, buildings, and the like, where persons and/or objects being tracked can be located. Other tracking systems supply position coordinates at which each tracked person and/or object is located, which in turn, can be mapped to physical and/or functional areas (zones) within the facility. The display of the present invention utilizes the zone concept to simplify the data for presentation to the system user.

For each person or object being tracked, the display of the present invention can utilize the following information from a tracking system:
 Name of the tracked person or object;
 Assigned zone (housing unit, hospital ward, etc.) for the tracked person or object;
 Time at which the tracked person or object first entered the zone in which the tracked person or object is currently present;
 Zone within which the tracked person or object is currently located;
 The status of the tracking device associated with the tracked person or object, if any, e.g., RFID battery status for a battery powered RFID tag;
 Time at which the tracked person or object was last located by the tracking system;
 Data indicating any alert conditions that the tracking system is capable of recognizing. For example,
  An indicator indicating whether a predetermined maximum elapsed time since the tracked person or object was last located by the tracking system has been exceeded. Additionally or alternatively, the time at which the tracked person or object was last located by the tracking system can be reported as a countdown timer showing the time remaining until the predetermined maximum elapsed time will occur and as the elapsed time since the predetermined maximum elapsed time was exceeded.
  An indicator indicating that a tracked person A and another tracked person B are located within the same zone when tracked person A and tracked person B are to be kept separated from one another.
  An indicator indicating that a tracked person or object is outside the zones within which the tracked person or object is permitted.
  An indicator indicating that a tracked person requires emergency support or a scheduled checkup.
  An indicator indicating that a tracked object is in need of maintenance or a scheduled checkup.
 Any other information to be displayed, such as identifying photographs, assigned bed number, other status and alert indicators, and the like.

The display of the present invention utilizes colors, graphics, and the physical grouping of related data on a display device, usually a computer monitor, to present tracking information in a compact and easily analyzed format. Data pertaining to a particular zone are segregated from other data, and similarly, data relative to each person within each zone are segregated or grouped, color-coded, and organized to make it easy to isolate all data in which a particular user is interested. Commonly used textual status, alert, and other indicators are replaced with small and easily recognizable icons, the definition of which become visible in a text "balloon" when the cursor is hovered over the icon in question. Different intensities of color fill or highlight and/or different fill or highlighting colors are used to indicate various potential problem levels. Data sorting and filtering features can be used to assure that data associated with such potential problems are easily isolated and viewed. Sorting can also be used to optimize the process of verifying the status of a person or object and the location by visual inspection. For example, sorting by housing unit and assigned bed allows for the easy correlation of an optimized inspector itinerary and the data provided by the tracking system. Together these features direct the attention of the system user to the main areas of concern and together these techniques reduce the area required on a monitor screen or other display device.

The display of the present invention represents each zone of the facility that is defined in the tracking system as a distinct area of the display device. Data pertaining to each tracked person or object are displayed in a distinct sub-area within the area representing the zone to which the particular person or object is assigned and in which the particular person or object is currently present. For example, if a tracked person is outside the zone to which he or she is assigned but is still within a zone where he or she is allowed, data fields within the area associated with the assigned zone and pertaining to the tracked person will contain the name of the zone in which he or she is currently located, and the name of the person's assigned or "Home" zone. All data pertaining to this particular tracked person will be highlighted to indicate an abnormal condition. Additionally, similar data pertaining to this person are displayed within the area representing the zone within which the person is currently located. All data pertaining to this person are highlighted in the same abnormal condition color within both zones, drawing attention to the fact that an abnormal condition exists. Other status conditions and corresponding colors and/or status icons are possible depending on the criteria of the specific facility and the capabilities of the associated tracking system.

Alerts regarding a given person or object being tracked operate as just described, but an icon indicating the highest severity level of all applicable alerts, if any, is placed in the "Sev" column of the display. Alerts are classified by severity level as either "Critical" or "Warning", with "Critical" being the most severe. When the cursor is hovered over the data record of a person or object to whom one or more alerts apply, details regarding the nature of the alert(s) appear in a small superimposed area known in the trade as a "tool tip" while the cursor remains positioned over the data record. Each alert is first created by the system in the unacknowledged state and optionally rendered to the system user with an acknowledgement indicator. When an alert is acknowledged, the identity of the acknowledging user and the time of acknowledgement are recorded and the related acknowledgement indicator is cleared. Alerts are typically acknowledged after the person or object and circumstances involved are checked by an officer. The number of "Critical" and "Warning" alerts that are currently unacknowledged in any given zone, if any, is displayed along with the zone name in the zone heading for that zone regardless of the display that is in use. In an alternate embodiment, each alert type, e.g., "not seen" alert, "keep separate" alert, "out of bounds" alert, or other alert condition detected by the tracking system, has a distinct icon and highlighting color.

The display of the present invention incorporates various controls that allow system users to customize the display according to their preference. There are two main display formats entitled "List" display view and "Record Cards" display view. It is possible for the records in either display format to have a thick red border when an unacknowledged alert exists for the associated person or object, a thin red border when acknowledged but active alerts and/or other predefined non-alert conditions exist, and no border when no predefined conditions exist.

When data within a given zone exist for tracked persons or objects, the "List" view display format presents these data as text and graphics in a format which is organized by rows and columns beneath a heading indicating the name of the zone. Data pertaining to each person or object being tracked occupy one row with each data field therein occupying one column in the display. The data rows pertaining to the persons or objects can be sorted according to any column by positioning the cursor over the column heading and clicking the left mouse button. The column order can also be changed according to system user preference by using the cursor to "drag and drop" column headings in the desired order. Rows are color coded to indicate various abnormal conditions and alert levels. Positioning the cursor over the row relating to a specific person or object and double clicking the left mouse button brings up a display of detailed information relating to that person, which includes a listing of arrival and departure times for the zone the person or object has visited.

The "Record Cards" view display format utilizes the same zone headings as previously described for the "List" view display format but the data are organized so as to relate to each tracked person or object (each row in the "List" view display format) into a virtual record card format in which data pertaining to the tracked person or object are displayed within the image of the record card with one person or object per record card. It should be noted that it is possible for multiple record cards to represent the same person or object, as in an assigned zone and a visited zone, but there is only one person or object per record card in every instance. In this case the record cards are colored with the same color and according to the same protocol as those previously discussed for the "List" view display format. The status and alert indicating icons previously discussed for the "List" view display format are used for the same purpose in the "Record Cards" view display format. This display format simulates the positioning of record cards each representing a particular tracked person or object, on a bulletin board, whiteboard, or other surface that is organized into areas representing the zones. The "Record Cards" view display format incorporates controls to allow data sorting and the inclusion and exclusion of certain data from the displayed record cards. For example, a small photograph of the person or object associated with each displayed record card may be shown, if desired, or in the interest of displaying more record cards in a given area the photograph and/or other information may be excluded from the displayed record cards. Similar to the "List" view display format, positioning the cursor over the record card relating to a specific person or object and double-clicking the left mouse button produces a display of detailed information relating to that person or object, which includes a history of arrival and departure times for zones the person or object has visited and any current alerts.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2A is an illustration of the display of the present invention in the "List" view display format, as in FIG. 2, and additionally illustrates the tool tip display describing an alert.

DESCRIPTION OF THE PREFERRED EMBODIMENT

The preferred embodiments of the present invention are shown in FIGS. 1 through 17. For simplicity sake, a tracking system providing only one type of alert, the "not seen" alert, and comprising three zones within a correctional facility having a population of six tracked inmates and an officer is shown. The zones consist of two housing units and a clinic, referred to as "Housing Unit 1", "Housing Unit 2" and "Clinic", respectively. Three inmates are assigned to each housing unit. John Doe, Stephen Jones and James Smith are inmates assigned to Housing Unit 1. Mark Brown, Scott Johnson and Frank Miller are inmates assigned to Housing Unit 2. A correctional officer, Thomas R. Turner, has no assigned zone location and roams freely throughout the correctional facility.

Figure 1:
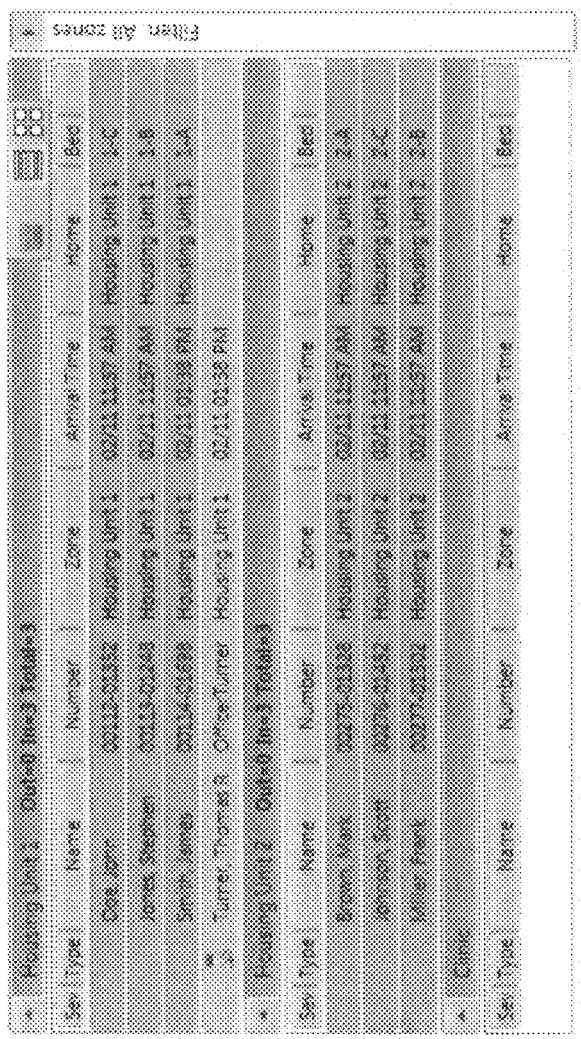
FIG. 1 is an illustration of the display of the present invention in the "List" view display format.

The display of the present invention in "List" view display format is illustrated in FIG. 1. The display format in this Figure can be changed between the "List" view and the "Record Card" view any time by positioning the cursor over the appropriate icon in the upper right hand corner of the display and clicking the left mouse button. Based on the color legend utilized, it can be readily seen that there are no abnormal conditions or alerts and all inmates are currently in their assigned housing units because all of the inmate rows are colored green. This is confirmed by the absence of any icons in the "Sev" column, which indicates the severity of any alerts that may be present. In addition, it is seen that Officer Thomas R. Turner is currently present in the "Housing Unit 1" zone. Officer Turner can be quickly identified as an officer based on the blue color of the row and the officer icon in the "Type" column of his record in the "Housing Unit 1" zone. The "Type" column contains icons indicating the classification of each tracked person, such as an officer or other staff personnel. Because inmates comprise the vast majority of tracked persons in correctional institutions, no icon is shown for inmates in the interest of display readability in this example. The absence of any "Type" icon indicates that the tracked person is an inmate. The "Name" column displays the name of each tracked person. The "Number" column displays an additional identifier associated with each tracked person. The "Status" column displays icons indicating the status, if any, of each tracked person. Depending on the particular facility these icons can indicate that the tracked person is a violent offender, is on suicide watch, or the like. The "Zone" column displays the name of the zone in which each tracked person is currently located. The "Arrival Time" column indicates the time at which each tracked person arrived in the zone shown in the "Zone" column. The "Home" column indicates the assigned zone for each tracked person. Additionally, each inmate's assigned bed identifier is shown in the "Bed" column.

Figure 2:
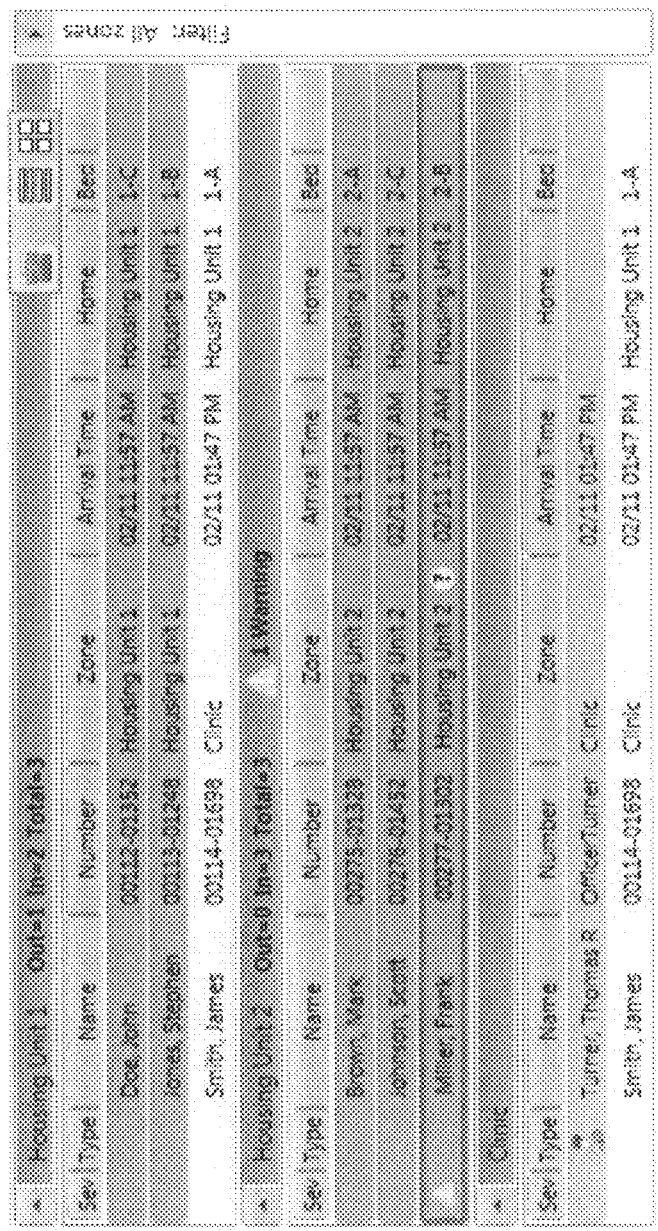
FIG. 2 is an illustration of the display of the present invention in the "List" view display format at a later time than in FIG. 1.

The situation in the correctional institution at a later time is illustrated in FIG. 2. In this case, the Figure illustrates the display after Officer Turner has escorted inmate Smith to the Clinic. Because inmate Smith is not in his assigned location of Housing Unit 1, his record within the Housing Unit 1 zone is highlighted in gray indicating that inmate Smith is out of his housing zone, per the color legend. Accordingly, "Clinic" is shown as his present location in the "Zone" column of inmate Smith's record. Similarly, inmate Smith's record appears a second time under the Clinic location, as previously described, Officer Turner is also shown as being in the Clinic, but since he has no assigned location, his record has moved from the area representing "Housing Unit 1" to the area representing the "Clinic".

Figure 2A:
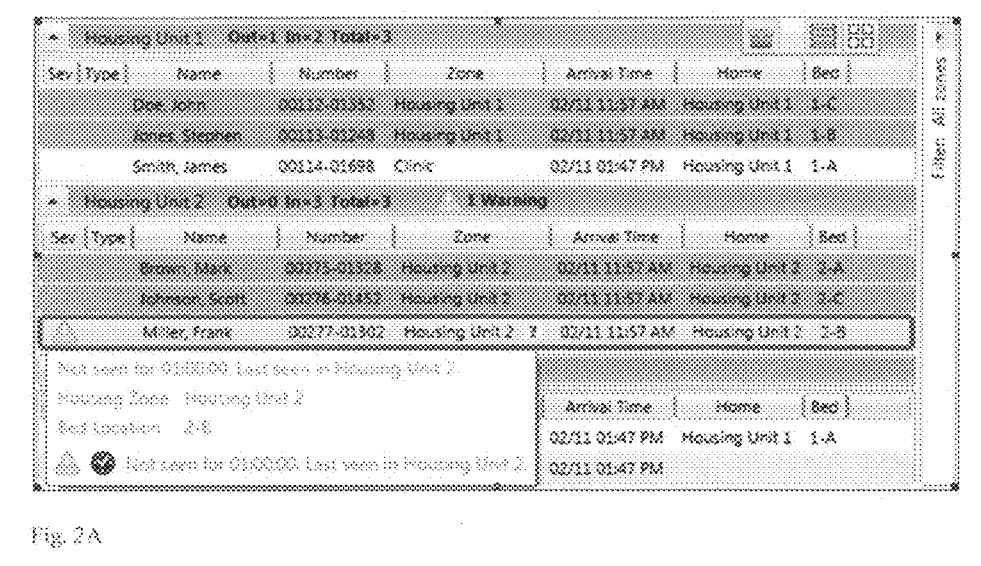

It is also seen in FIG. 2 that inmate Frank Miller's record appears with a thick red border and on a green background, indicating that a potentially important event has occurred. The warning icon is shown in the "Sev" column of inmate Miller's record to indicate that an alert with a "warning" severity level exists for this inmate. Hovering the cursor over inmate Miller's data record produces the tool tip display shown in FIG. 2A, which describes the nature of the alert. From the foregoing it is apparent that more than a predetermined period of time has elapsed since this inmate was located by the system (Not Seen Alert). The "Zone" column continues to show inmate Miller as being in his assigned "Home" housing unit since he has not been found elsewhere by the tracking system. The situation could be an indication that the inmate's tracking device (RFID tag, or the like) is no longer functional, or the inmate has spent longer than the predetermined period of time in an area not "visible" to the tracking system. For example, systems using RFID tags may have areas that are not within the range of any antenna of the tracking system. Regardless, the alert represents a condition that must be brought to the attention of the correctional facility's staff.

The present invention has the ability to collapse the display of individual zones shown in FIGS. 1 and 2 such that only the zone heading is displayed. To accomplish the foregoing, the cursor is moved to the arrow button shown in the far left end of the zone headings and the left mouse button is clicked. Once collapsed, a given zone can be expanded using the same control.

Figure 3:
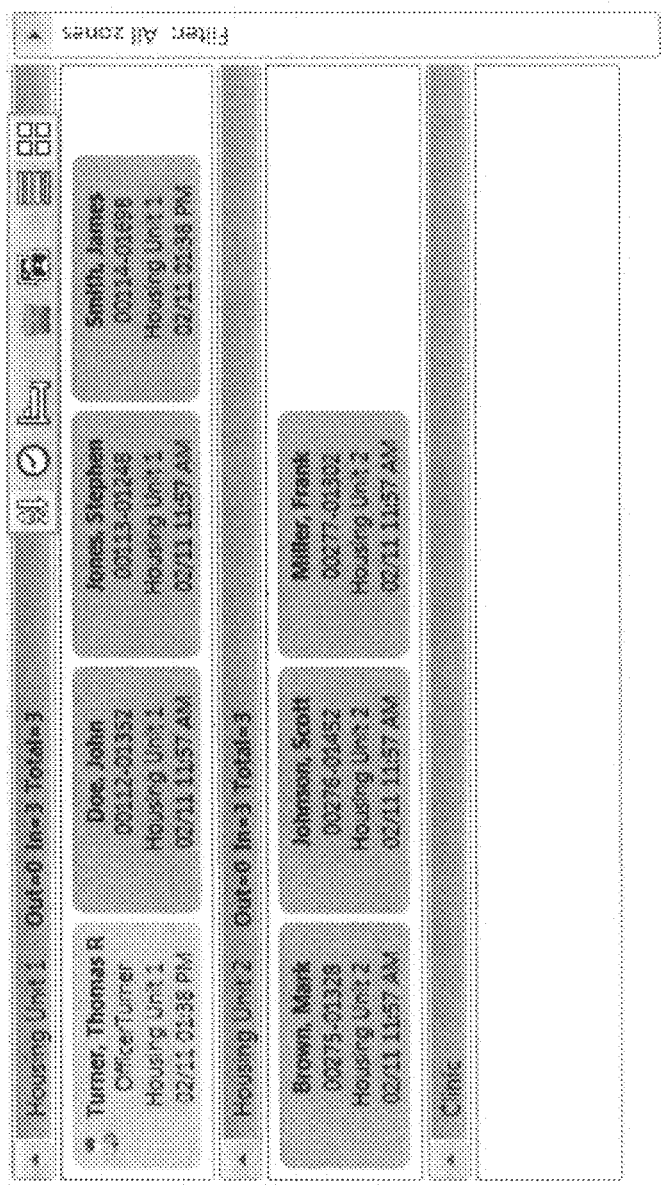
FIG. 3 is an illustration of the display of the present invention in the "Record Cards" view display format for the inmate data displayed in FIG. 1.
Figure 4:
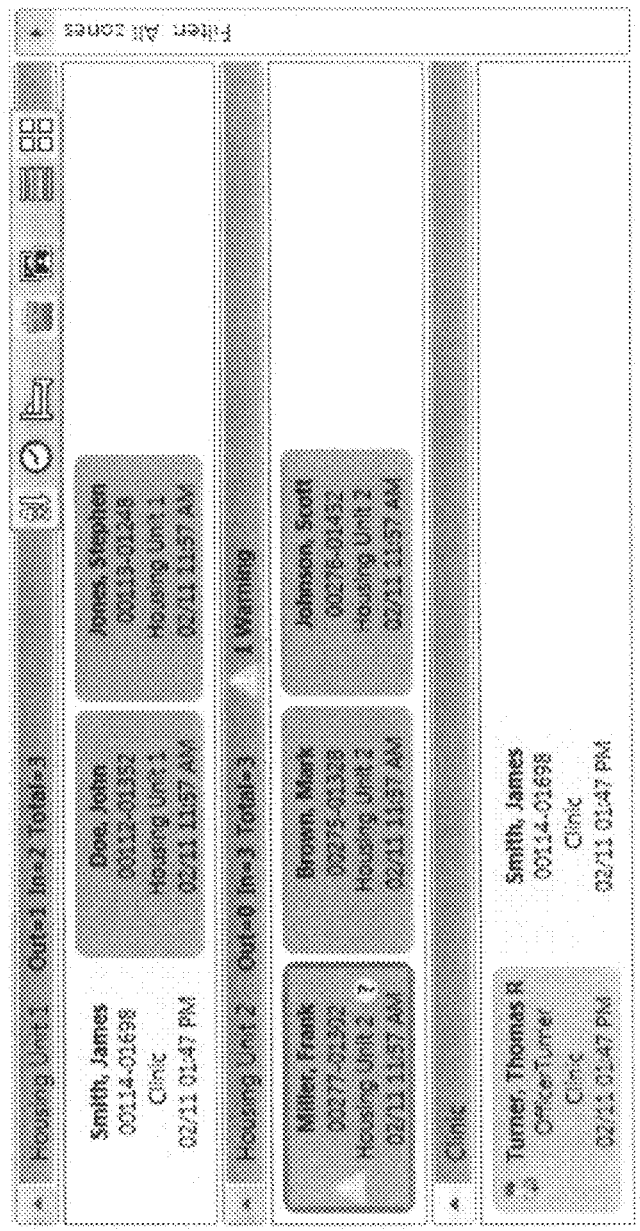
FIG. 4 is an illustration of the display of the present invention in the "Record Cards" view display format for the inmate data displayed in FIG. 2.
Figure 5:
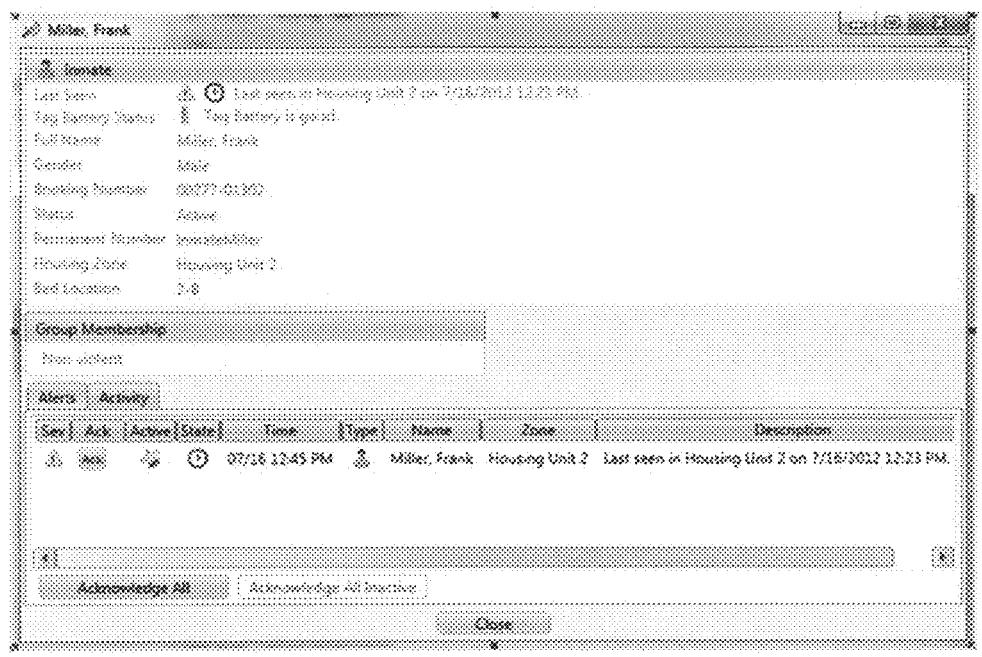
FIG. 5 is an illustration of a pop-up dialog display of the present invention showing detailed information which can be produced from the "List" view display format or the "Record Cards" view display format.

FIGS. 3 and 4 show the "Record Cards" view display format for the inmates and the officer in previously described FIGS. 1 and 2, respectively, with a minimal set of data displayed within the cards. In the "List" view or the "Record Cards" view display format, double clicking on a record (a row in the "List" view or a card in the "Record Cards" view) associated with any tracked inmate produces a pop-up display of detailed information relating to that inmate. An example of the foregoing is illustrated in FIG. 5. The display in FIG. 5 also permits acknowledging alerts relating to the inmate for whom the data are displayed.

Figure 6:
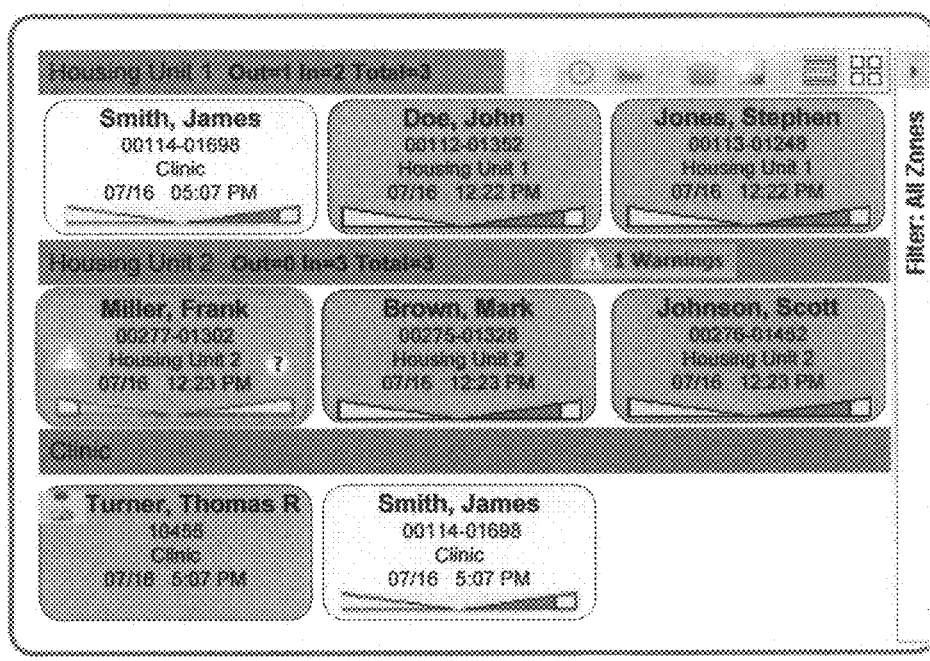
FIG. 6 is an illustration of a display of the present invention in the "Record Cards" view display format shown in FIG. 4 that additionally includes a graphical indication as to the time remaining until a predetermined maximum elapsed time will occur since the last time the location of an inmate was determined and/or the elapsed time since the aforementioned predetermined maximum elapsed time was exceeded.

Additionally or alternatively, the "last read" time along with a predetermined maximum elapsed time can be used to display a small graph in the "Record Cards" view display format showing the time remaining until the predetermined maximum elapsed time will have occurred, and the elapsed time since the predetermined maximum elapsed time was exceeded, as previously discussed. FIG. 6 shows the appearance of FIG. 4 when such an alternative has been implemented. The display in FIG. 6 permits officials to anticipate "Not Seen" alerts at a glance.

Figure 7:
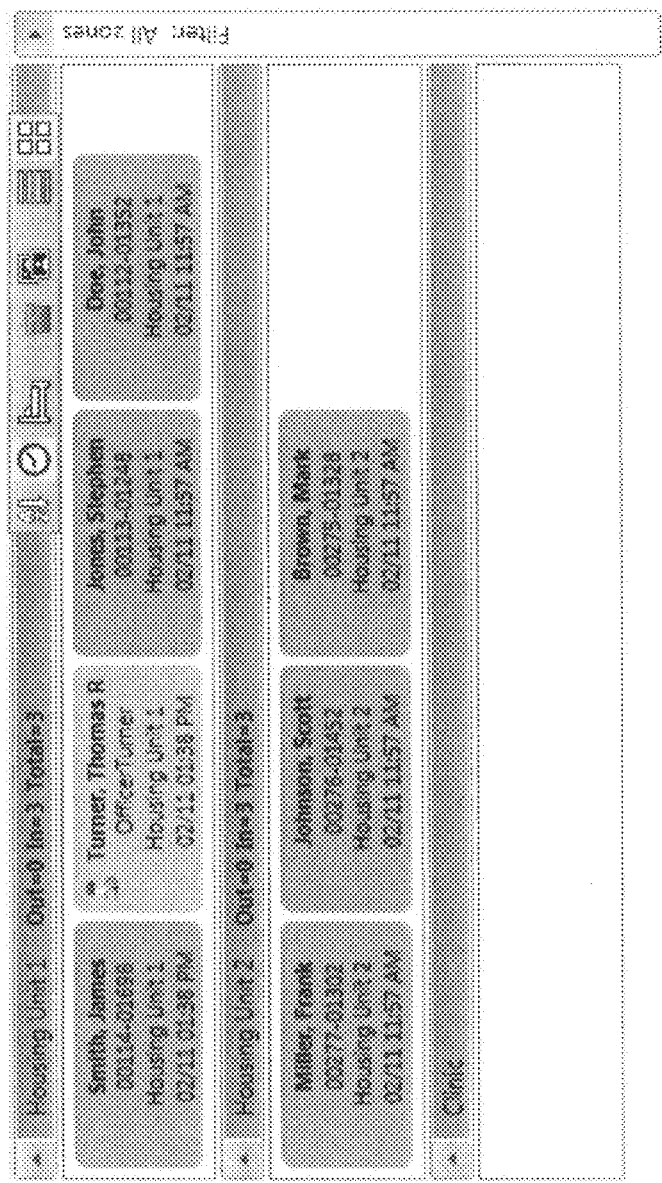
FIG. 7 is an illustration of a display of the present invention in the "Record Cards" view display format and shows the record cards after being sorted through activation of the time ordering button.
Figure 8:
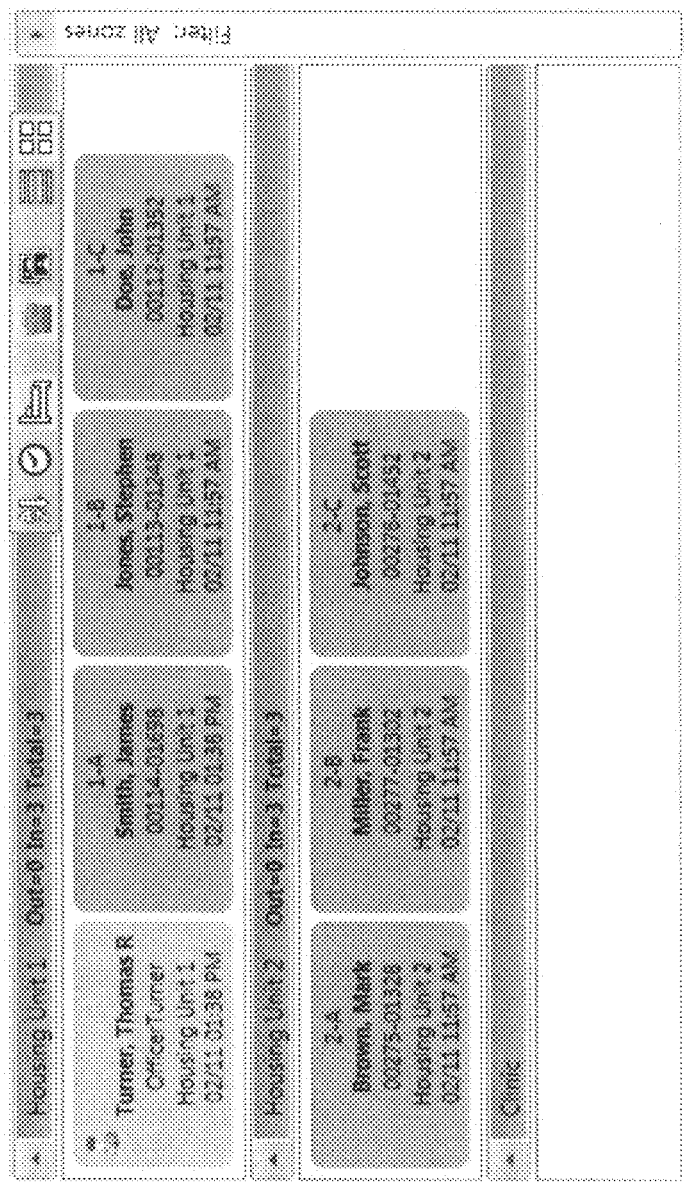
FIG. 8 is an illustration of a display of the present invention in the "Record Cards" view display format and shows the record cards after being sorted through activation of the bed number ordering button.
Figure 9:
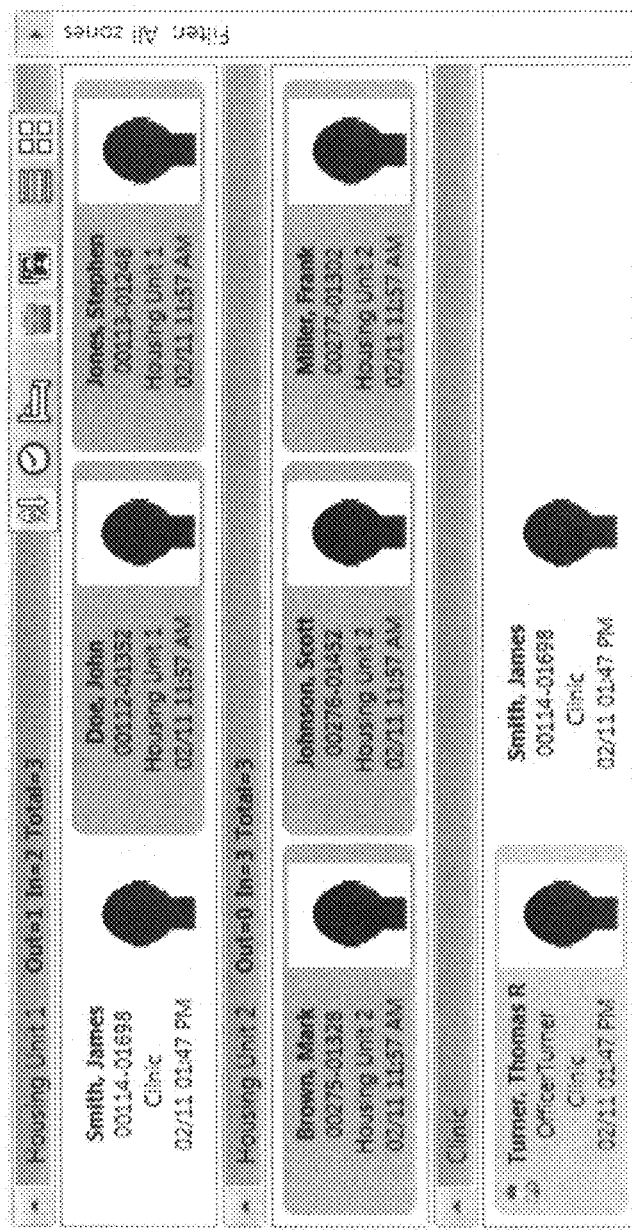
FIG. 9 is an illustration of a display of the present invention in the "Record Cards" view display format and shows the record cards after activation of the photo display button causing each record card to include a photograph of the person associated with the respective record card.
Figure 10:
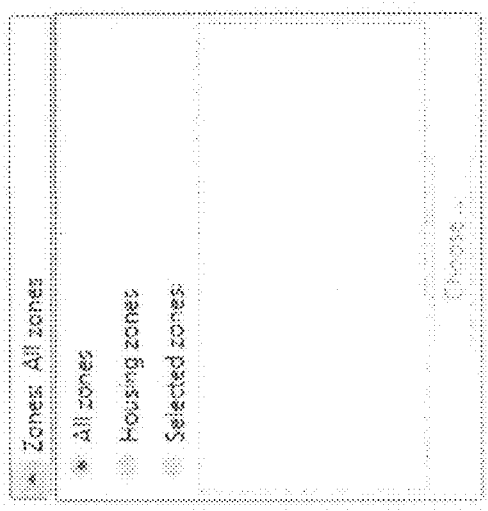
FIG. 10 is an illustration of a display of the present invention and shows the filter controls associated with the present invention.
Figure 11:
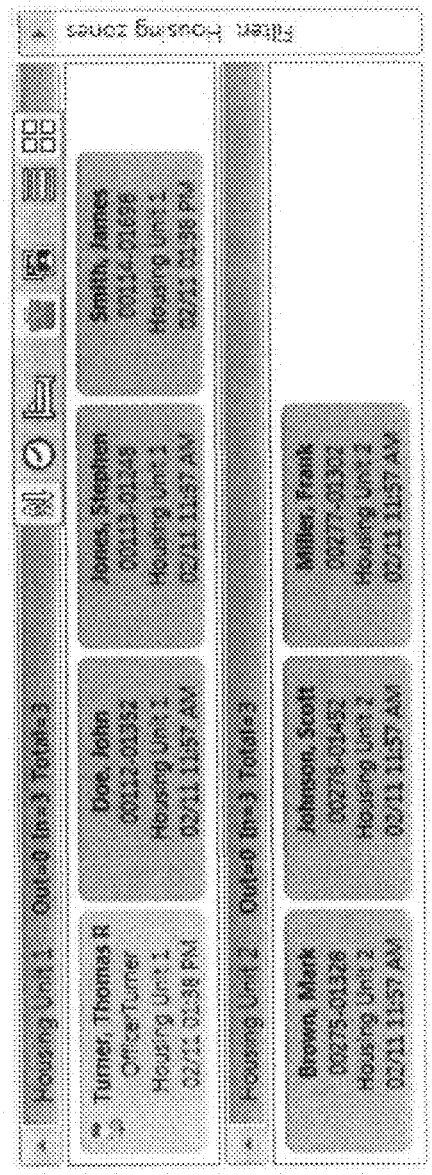
FIG. 11 is an illustration of a display of the present invention in the "Record Cards" view display format for the inmate data displayed in FIGS. 1 and 3 after the "Housing Zone" filter in FIG. 10 has been selected.
Figure 12:
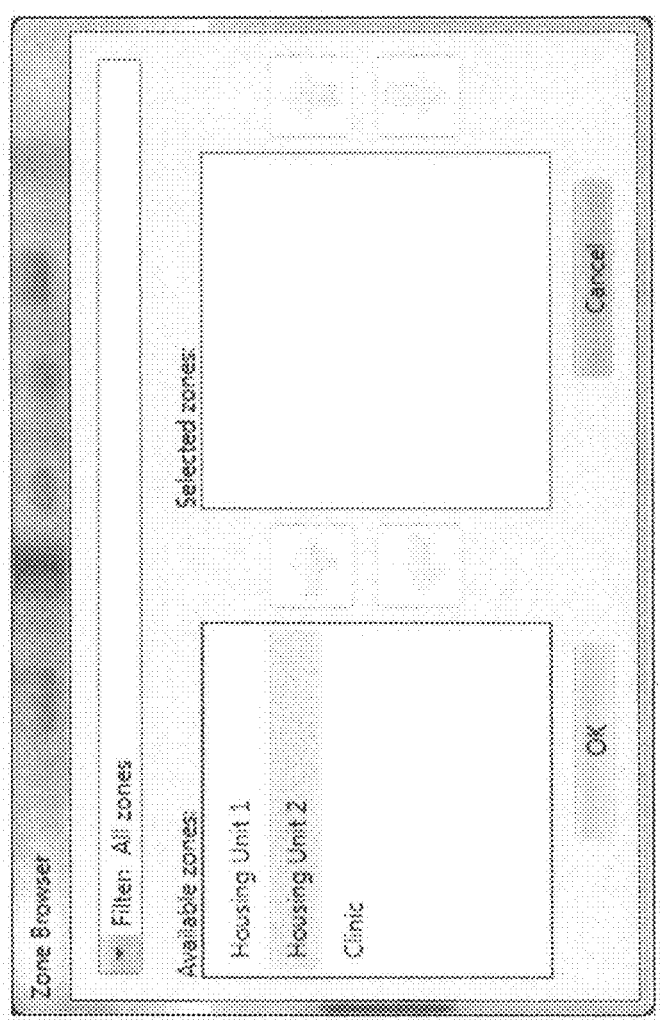
FIG. 12 is an illustration of a display of the present invention showing the Zone Browser after the "Selected Zones" filter in FIG. 10 has been selected.

The "Record Cards" view display format provides button-style controls located to the left of the "List" view icon in the upper right hand corner that allows data sorting and the inclusion or the exclusion of certain data from the displayed record cards. In order, from left to right, the buttons are the default sort ordering button, time ordering button, bed number ordering button, include assets (objects) button, and photo display button. Except for the default sort ordering button, these are self-explanatory. The default sort ordering button causes the display order to be as follows:

1. Officers with alerts, alphabetically
2. Assets (objects) with alerts, alphabetically
3. Inmates with alerts, alphabetically
4. Officers with no alerts, alphabetically
5. Assets (objects) with no alerts, alphabetically
6. Inmates with no alerts, alphabetically Each button is activated by positioning the cursor over the button and clicking the left button on the mouse. The default sort ordering button, time ordering button, and bed number ordering button control the ordering of the data and their operation is mutually exclusive. The photo display button can be combined with any one of these three ordering buttons as will be discussed further herein. When deactivation of one of these four control buttons is possible, it is accomplished by placing the cursor over the activated button and clicking the left button on the mouse. When activated, the default sort ordering button sorts the record cards, left to right and top to bottom, in the previously described default order, as shown in FIG. 3. The time ordering button sorts the record cards, left to right and top to bottom, according to the most recent time at which the inmate associated with the record card arrived in the given zone, as shown in FIG. 7. The bed number ordering button expands the displayed record cards to include the bed number of the inmate associated with each record card and sorts the record cards, left to right and top to bottom, in order according to the assigned bed number, as shown in FIG. 8. The photo display button expands each displayed record card to include a small photograph of the inmate associated with the respective record card, and orders the cards while maintaining the last chosen record card ordering method, the default being left to right and top to bottom in the previously described default order according to the inmate's surname as it appears on the record card, as shown in FIG. 9. The photo display button can be used in combination with any of the three ordering buttons to change the ordering of the record cards while each such record card displays a photograph of the associated inmate. For example, clicking on the photo display button and then clicking on the bed number ordering button produces a display in which the record cards show photographs of the inmate associated with each order according to the bed assigned to the associated inmate.

Figure 13:
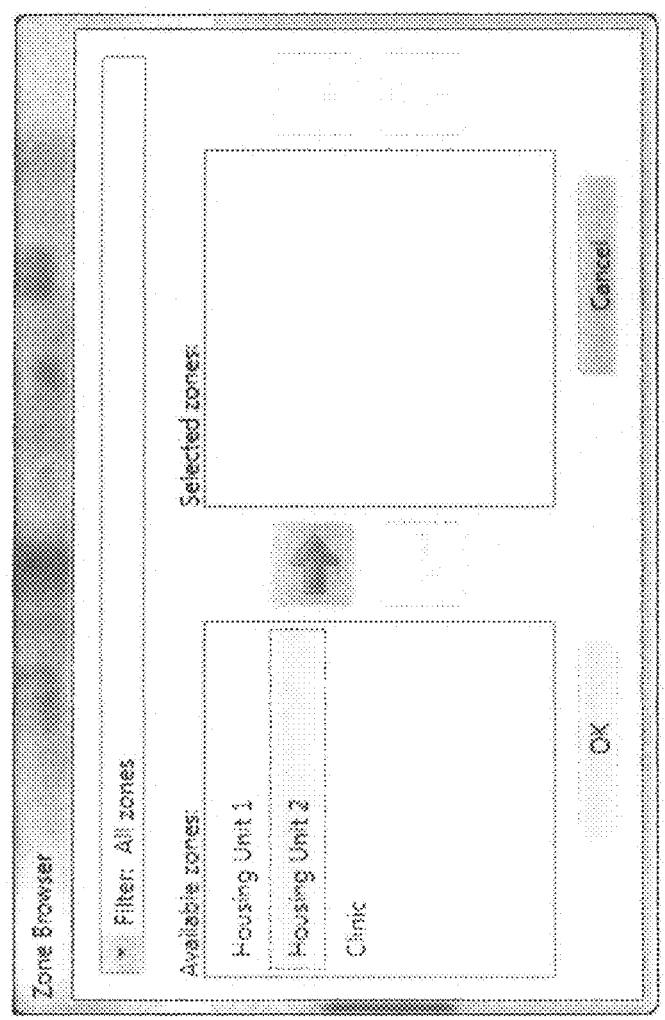
FIG. 13 is an illustration of a display of the present invention showing the Zone Browser after "Housing Unit 2" identifier has been selected thereon.
Figure 14:
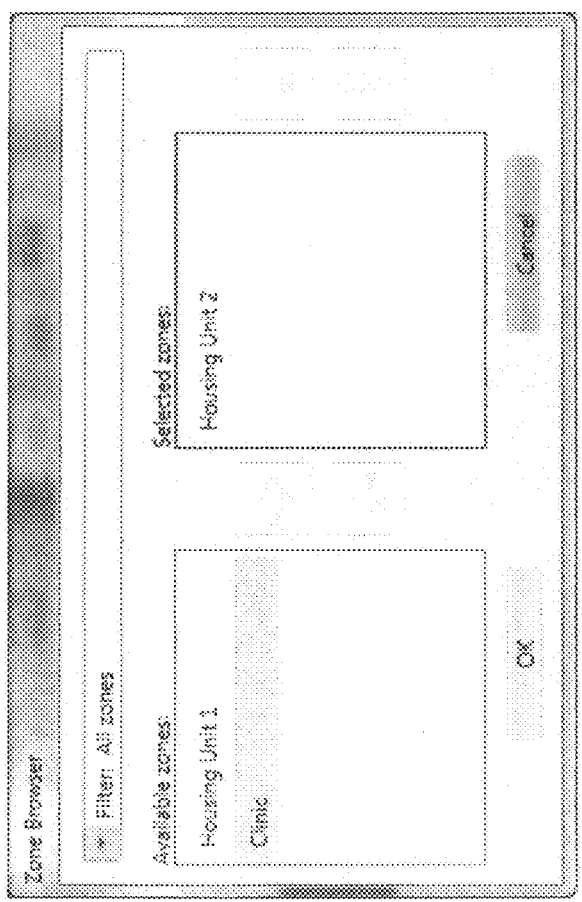
FIG. 14 is an illustration of a display of the present invention showing the Zone Browser after the "Housing Unit 2" identifier has been selected and "Housing Unit 2" has been moved into the "Selected Zone" area of the display.
Figure 15:
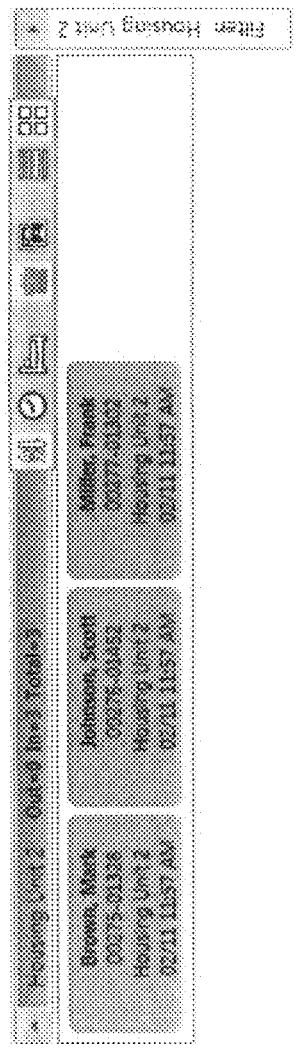
FIG. 15 is an illustration of a display of the present invention resulting from the filter selection in FIG. 14.

Both the "List" view and the "Record Cards" view display formats have the ability to filter data in various manners. The same controls are used for filtering regardless of the views being used. This filtering permits tracking system users to restrict the data displayed to specific zones or categories of zones. Positioning the cursor over the arrow at the top of the vertical filtering bar located on the right side of either the "List" view or "Record Cards" view display formats provides access to the filtering controls shown in FIG. 10. Selecting "All Zones" provides a display of all zones available, as shown in FIG. 1 or 3, depending on whether the "List" view or "Record Cards" view display format is selected. Selecting "Housing Zones" limits the display to the housing units. For example, applying the "Housing Zones" filter to the display shown in FIG. 3 results in the display shown in FIG. 11. Selecting the "Selected Zones" filter choice provides the Zone Browser shown in FIG. 12. The Zone Browser permits zone identifiers to be moved between the "Available Zones" to the "Selected Zones" areas of the Zone Browser by means of the two arrow buttons located between these areas. For example, selecting the "Housing Unit 2" zone identifier in the "Available Zone" area and then clicking on the right pointing arrow moves the "Housing Unit 2" zone identifier in to the "Selected Zones" area, as shown in FIGS. 13 and 14. When zone identifiers appear in the "Selected Zones" area of the control, only those zones will appear in the resulting "List" view and "Record Cards" view display formats. For example, FIG. 15 shows the display resulting from the filter selection shown in FIG. 14.

Figure 16:
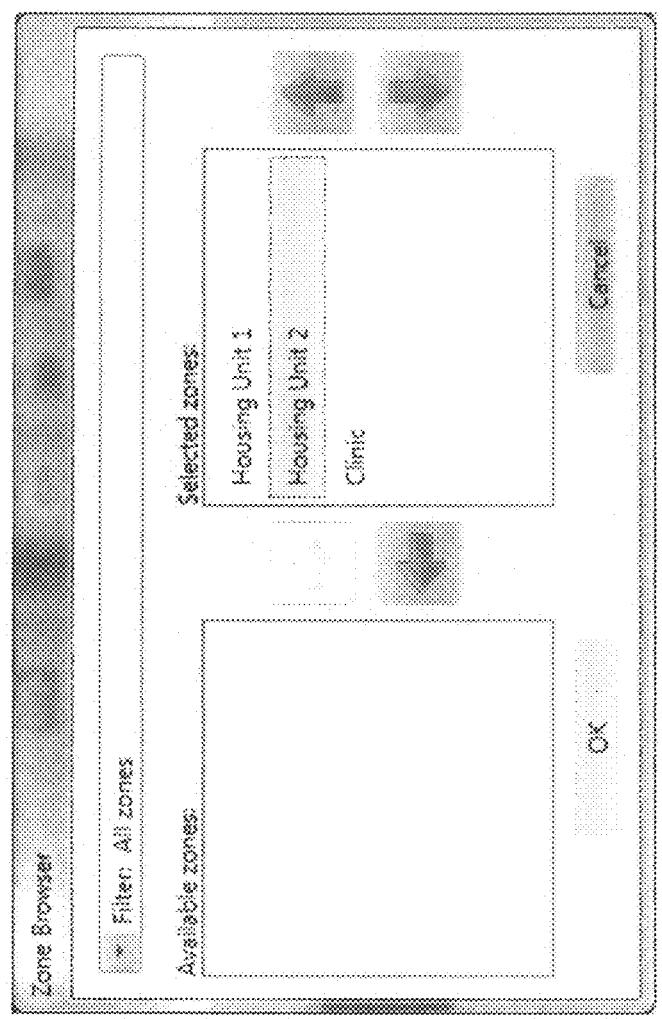
FIG. 16 is an illustration of a display of the present invention showing the Zone Browser after multiple zone identifiers have been selected and such multiple zones have been moved into the "Selected Zones" area of the display.

When multiple zones appear in the "Selected Zones" area of the control, the upward and downward pointing arrows on the right side of the control can be used to change the order of the zones displayed. To accomplish the foregoing, one or more of the zone identifiers in the "Selected Zones" area is selected with the cursor, as shown in FIG. 16. The upward pointing arrow can then be used to place the selected zone identifier earlier in the display order, or the downward pointing arrow can then be used to place the selected zone identifier later in the display order. Alternate embodiments of the present invention permit the ordering of zones directly on the whiteboard display view "up" and "down" buttons on each display header.

Figure 17:
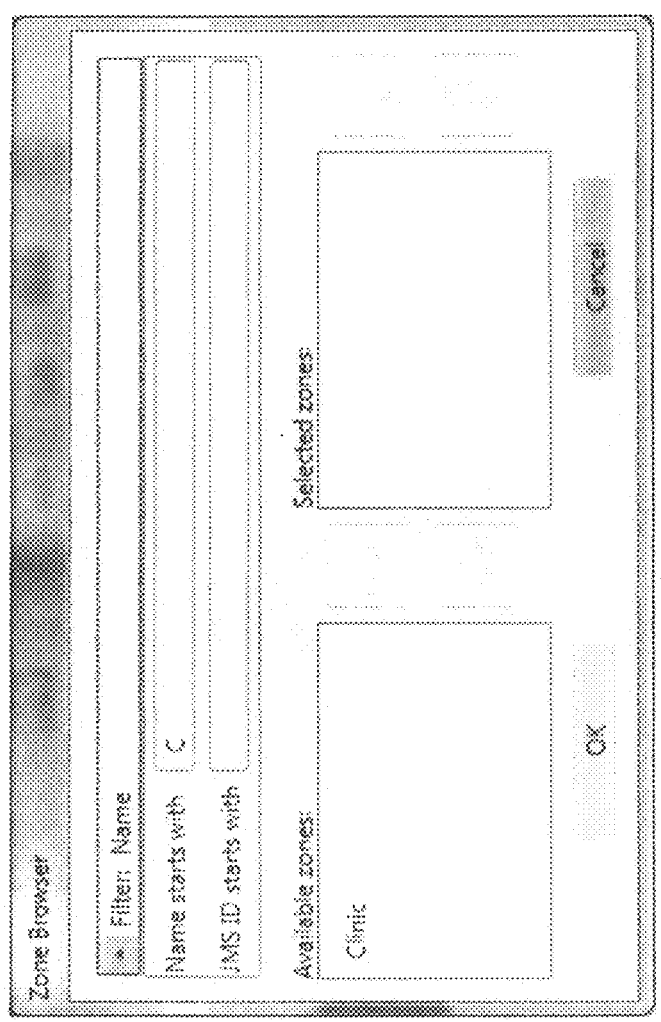
FIG. 17 is an illustration of a display of the present invention showing the Zone Browser after the filtering of zones according to the first letters of the zone name.

Additionally, clicking in the field that displays the filter selection at the top of the Zone Browser enables the filtering of zones according to the first letters (any number of letters can be specified) of the zone name or by an identifier assigned to the zone, as shown in FIG. 17. In correctional settings, JMS (Jail Management System) identifiers are often used. An example of setting the filter to select only zone names beginning with the letter "C" is shown in FIG. 17.

Certain modifications and improvements will occur to those skilled in the art upon reading the foregoing. It is understood that all such modifications and improvements have not been included herein for the sake of conciseness and readability, but are properly within the scope of the following claims.

We claim:

1. A display for presenting information comprising data relating to persons or objects of interest, said data being presented on a surface in one of a plurality of predetermined planar formats, said surface being divided into sections, each of said sections containing sub-sections that contain data relating to persons or objects located within a particular area, said predetermined planar formats being changeable from a first format showing said sub-sections in a first arrangement to a second format showing said sub-sections in a second arrangement, one of said predetermined planar formats showing said sub-sections in a listing format which lists said person or object according to the names of said persons or objects, the order in which said persons or objects are listed being changeable.

2. A display for presenting information comprising data relating to persons or objects of interest, said data being presented on a surface in one of a plurality of predetermined planar formats, said surface being divided into sections, each of said sections containing sub-sections that contain data relating to persons or objects located within a particular area, said predetermined planar formats being changeable from a first format showing said sub-sections in a first arrangement to a second format showing said sub-sections in a second arrangement, one of said predetermined planar formats showing said sub-sections in a record card format, each of said persons or objects having a record card assigned thereto, said record cards being arranged according to the names of said persons or objects.

3. A display for presenting information comprising data relating to persons or objects of interest, said data being presented on a surface in one of a plurality of predetermined planar formats, said surface being divided into sections, each of said sections containing sub-sections that contain data relating to persons or objects located within a particular area, said predetermined planar formats being changeable from a first format showing said sub-sections in a first arrangement to a second format showing said sub-sections in a second arrangement, one of said predetermined planar formats showing said sub-sections in a record card format, each of said persons or objects having a record card assigned thereto, said record cards being arranged according to the names of said persons or objects, the order in which said record cards of said persons or objects are displayed being changeable.

4. A display for presenting information comprising data relating to persons or objects of interest, said data bring presented on a surface in one of a plurality of predetermined planar formats, said surface being divided into sections, each of said sections containing sub-sections that contain data relating to persons or objects located within a particular area, said predetermined planar formats being changeable from a first format showing said sub-sections in a first arrangement to a second format showing said sub-sections in a second arrangement, one of said predetermined planar formats showing said sub-sections in a record card format, each of said persons or objects having a record card assigned thereto, said record cards being arranged according to the names of said persons or objects, said record cards including a graphical representation as to the time remaining until a predetermined maximum time has elapsed since the location of said person or object has been determined.

5. A display for presenting information comprising data relating to persons or objects of interest, said data being presented on a surface in one of a plurality of predetermined planar formats, said surface being divided into sections, each of said sections containing sub-sections that contain data relating to persons or objects located within a particular area, said predetermined planar formats being changeable from a first format showing said sub-sections in a first arrangement to a second format showing said sub-sections in a second arrangement, one of said predetermined planar formats showing said sub-sections in a record card format, each of said persons or objects having a record card assigned thereto, said record cards being arranged according to the names of said persons or objects, said record cards including a graphical representation as to the time that has elapsed after a predetermined maximum time has been exceeded since the location of said person or object has been determined.

6. A display for presenting information comprising data relating to persons or objects of interest, said data being presented on a surface in one of a plurality of predetermined planar formats, said surface being divided into sections, each of said sections containing sub-sections that contain data relating to persons or objects located within a particular area, said predetermined planar formats being changeable from a first format showing said sub-sections in a first arrangement to a second format showing said sub-sections in a second arrangement, said first arrangement being a listing format of said persons or objects.

7. A display for presenting information comprising data relating to persons or objects of interest, said data being presented on a surface in one of a plurality of predetermined planar formats, said surface being divided into sections, each of said sections containing sub-sections that contain data relating to persons or objects located within a particular area, said predetermined planar formats being changeable from a first format showing said sub-sections in a first arrangement to a second format showing said sub-sections in a second arrangement, said second arrangement being a listing format of said persons or objects.

8. A display for presenting information comprising data relating to persons or objects of interest, said data being presented on a surface as a two-dimensional representation in one of a plurality of predetermined formats, said surface being divided into sections, each of said sections containing sub-sections that contain data relating to persons or objects located within a particular area, said two-dimensional representation of predetermined formats being changeable from a first format showing said sub-sections in a first arrangement to a second format showing said sub-sections in a second arrangement, one of said predetermined formats showing said sub-sections in a record card format, each of said persons or objects having a record card assigned thereto, said record cards being arranged according to the names of said persons or objects.

9. A display for presenting information comprising data relating to persons or objects of interest, said data being presented on a surface as a two-dimensional representation in one of a plurality of predetermined formats, said surface being divided into sections, each of said sections containing sub-sections that contain data relating to persons or objects located within a particular area, said two-dimensional representation of predetermined formats being changeable from a first format showing said sub-sections in a first arrangement to a second format showing said sub-sections in a second arrangement, one of said predetermined formats showing said sub-sections in a record card format, each of said persons or objects having a record card assigned thereto, said record cards being arranged according to the names of said persons or objects, the order in which said record cards of said persons or objects are displayed being changeable.

10. A display for presenting information comprising data relating to persons or objects of interest, said data being presented on a surface as a two-dimensional representation in one of a plurality of predetermined formats, said surface being divided into sections, each of said sections containing sub-sections that contain data relating to persons or objects located within a particular area, said two-dimensional representation of predetermined formats being changeable from a first format showing said sub-sections in a first arrangement to a second format showing said sub-sections in a second arrangement, one of said predetermined formats showing said sub-sections in a record card format, each of said persons or objects having a record card assigned thereto, said record cards being arranged according to the names of said persons or objects, said record cards including a graphical representation as to the time remaining until a predetermined maximum time has elapsed since the location of said person or object has been determined.

11. A display for presenting information comprising data relating to persons or objects of interest, said data being presented on a surface as a two-dimensional representation in one of a plurality of predetermined formats, said surface being divided into sections, each of said sections containing sub-sections that contain data relating to persons or objects located within a particular area, said two-dimensional representation of predetermined formats being changeable from a first format showing said sub-sections in a first arrangement to a second format showing said sub-sections in a second arrangement, one of said predetermined formats showing said sub-sections in a record card format, each of said persons or objects having a record card assigned thereto, said record cards being arranged according to the names of said persons or objects, said record cards including a graphical representation as to the time that has elapsed after a predetermined maximum time has been exceeded since the location of said person or object has been determined.

12. A display for presenting information comprising data relating to persons or objects of interest, said data being presented on a surface as a two-dimensional representation in one of a plurality of predetermined formats, said surface being divided into sections, each of said sections containing sub-sections that contain data relating to persons or objects located within a particular area, said two-dimensional representation of predetermined formats being changeable from a first format showing said sub-sections in a first arrangement to a second format showing said sub-sections in a second arrangement, said first arrangement being a listing format of said persons or objects.

13. A display for presenting information comprising data relating to persons or objects of interest, said data being presented on a surface as a two-dimensional representation in one of a plurality of predetermined formats, said surface being divided into sections, each of said sections containing sub-sections that contain data relating to persons or objects located within a particular area, said two-dimensional representation of predetermined formats being changeable from a first format showing said sub-sections in a first arrangement to a second format showing said sub-sections in a second arrangement, said second arrangement being a listing format of said persons or objects.

14. A display for presenting information comprising data relating to persons or objects of interest, said data being presented on a surface as a two-dimensional representation in one of a plurality of predetermined formats, said surface being divided into sections, each of said sections containing sub-sections that contain data relating to persons or objects located within a particular area, said two-dimensional representation of predetermined formats being changeable from a first format showing said sub-sections in a first arrangement to a second format showing said sub-sections in a second arrangement, one of said predetermined formats showing said sub-sections in a listing format which lists said person or object according to the names of said persons or objects, the order in which said persons or objects are listed being changeable.

* * * * *